United States Patent [19]

Morita et al.

[11] 3,959,345
[45] May 25, 1976

[54] PRODUCTION OF MALEONITRILE

[75] Inventors: Katsura Morita; Naoto Hashimoto; Koichi Matsumura, all of Osaka, Japan

[73] Assignee: Takeda Chemical Industries, Ltd., Osaka, Japan

[22] Filed: Jan. 30, 1975

[21] Appl. No.: 545,395

[30] Foreign Application Priority Data

Feb. 18, 1974 Japan............................. 49-19669

[52] U.S. Cl............................................. 260/465.8 R
[51] Int. Cl.²...................................... C07C 120/00
[58] Field of Search........................... 260/465.8 R

[56] References Cited
UNITED STATES PATENTS

| | | | |
|---|---|---|---|
| 2,385,469 | 9/1945 | Salley | 260/465.3 |
| 2,385,470 | 9/1945 | Salley et al. | 260/465.3 |
| 2,399,349 | 4/1946 | Hochwalt | 260/465.8 R |
| 2,471,767 | 5/1949 | Mowry et al. | 260/465.8 R |
| 3,070,622 | 12/1962 | Martin | 260/465.8 R |

OTHER PUBLICATIONS

Murahashi, et al.; C. A., 53, 1959, 5163f.

Primary Examiner—Joseph P. Brust
Attorney, Agent, or Firm—Burgess, Ryan and Wayne

[57] ABSTRACT

Maleonitrile is obtained as a dominant product of the reaction between cyanoacetylene and hydrogen cyanide. The yield of maleonitrile is remarkably higher than that in any of known processes.

11 Claims, No Drawings

PRODUCTION OF MALEONITRILE

This invention relates to a method for producing maleonitrile.

Maleonitrile is useful as a synthetic intermediate for the production of pharmaceuticals (e.g. pyridoxine and its related compounds), industrial chemicals and other various useful compounds such as 3- or 5-amino-isoxazoles, nitrogen-containing compounds (e.g. purine bases, pyrimidine bases), and a starting monomer for the polymer synthesis.

Among known processes for the production of maleonitrile, the following three are given as its typical ones:

1. Bulletin de la Societe Chemique de Belgique, Tome 46 (1937) 199 discloses a process for producing maleonitrile in which with is reacted with cuprous cyanide with heating at a temperature of about 100°C. In this process, however, the dominant product is not maleonitrile but fumaronitrile, so that the yield of maleonitrile is quite low and this process inevitably requires a further process for separation.

2. Journal of Organic Chemistry 10, 155(1945) discloses a process for the production of maleonitrile in which maleamide is subjected to dehydration with phosphorous pentoxide. In this process, the yield of maleonitrile is reported as low as only 39% of the theoretical amount even in its crude product.

The author of Journal of Chemical Society 1952, 4839 reported, as the results of his follow-up experiment, that the yield of maleonitrile in the process is very low. Further the synthesis of maleamide is difficult so that this process is not a practical one.

3. Journal of Chemical Society 1952, page 4840 presents a process comprising the dehydration of maleamide with phosphorous oxychloride. This process also has drawbacks in practical application, because firstly the synthesis of the starting material maleamide is difficult and secondly the reaction proceeds only under strictly controlled conditions, and the yield of maleonitrile is as low as 40% of the theoretical yield at maximum.

As is illustrated above, there has not been reported any method for the production of maleonitrile applicable to industrial purposes.

In an attempt to overcome the drawbacks in these known processes and to provide a new process for specifically producing maleonitrile, the present inventors made extensive studies which culminated in a remarkably surprising discovery of a fact that the addition of hydrogen cyanide to the carbon-carbon triple bond of cyanoacetylene occurs stereospecifically in a trans-fashion to give maleonitrile with a satisfactory yield. Further, in this reaction, the obtained maleonitrile appears in high purity, because the reaction proceeds with negligible side reactions. This invention is the result of the above finding and subsequent research.

This invention is, thus, a method for producing maleonitrile characterized by the reaction between cyanoacetylene and hydrogen cyanide.

Hydrogen cyanide is preferably employed in its liquid state. Hydrogen cyanide may also be used in the form of a composition convertible into hydrogen cyanide in the reaction system. In the latter case, the composition may be, for example, the mixture of cyanides (e.g. sodium cyanide, potassium cyanide, acetonecyanohydrin) with acids (e.g. hydrochloric acid, sulfuric acid, acetic acid, phosphoric acid) or with bases (e.g. sodium carbonate, sodium bicarbonate).

While the proportion of hydrogen cyanide to cyanoacetylene in the reaction mixture is widely optional, use of a slightly excess amount of hydrogen cyanide relative to cyanoacetylene, namely about one to two moles in terms of hydrogen cyanide per mole of cyanoacetylene, is preferred.

The reaction more smoothly proceeds in a liquid phase. The starting hydrogen cyanide itself is liquid at a temperature above −13.3°C, and therefore the reaction occurs without employing a solvent. But in a solvent, the side reactions can be rather suppressed with a result that maleonitrile is recovered in a high purity. The solvent should be such that it that does not react with any of both the reactants under the conditions. Thus, for example, organic solvents such as acetonitrile, methylene chloride, chloroform, diethyl ether, tetrahydrofuran, dioxane, ethyl acetate, acetic acid, dimethylformamide, dimethylsulfoxide, benzene, etc. and water or their mixtures may be optionally employed.

While there is not particular limitation upon the reaction temperature, a convenient temperature within the range of −20° to 100°C is to be recommended, and, within the above range, a room temperature (about 0°C to 30°C) is most preferred.

Under such conditions as mentioned above the reaction proceeds smoothly and usually ends within a rather short period of time, i.e. 0.5 to 24 hours.

There are cases in which the reaction of this invention proceeds more satisfactorily in the presence of an acid substance, a basic substance or a salt as a catalyst. As the acid substance, there may be mentioned, for example, so-called Lewis acid (e.g. anhydrous aluminium chloride and, potassium bifluoride) and so on. As the basic substance, there may be mentioned, for example, inorganic or organic bases, such as alkali metal hydroxide (e.g. sodium hydroxide, potassium hydroxide and lithium hydroxide), organic amine (e.g. triethylamine, N-methylmorpholine and 1-methylpyrazole) and so on. As the salt, use may be made, for example, of quaternary ammonium salts (e.g. tetraethylammonium chloride, tetraethylammonium bromide, tetraethylammonium iodide, benzyltrimethylammonium chloride, benzyltrimethylammonium bromide, benzyltrimethylammonium iodide, etc.), neutral to weakly basic inorganic salts (for example, alkali metal halide (e.g. lithium chloride, lithium bromide, lithium fluoride, potassium iodide, potassium fluroride, sodium fluoride and cesium fluoride), mineral acid salt of an aklali metal (e.g. lithium nitrate, lithium sulfate, potassium cyanide, sodium cyanide, potassium thiocyanate, lithium carbonate, sodium carbonate and potassium carbonate), ammonium salt (e.g. ammonium carbonate and ammonium acetate), and other kinds of salt (e.g. sodium acetate, potassium acetate, potassium formate, potassium ferricyanide and aluminum isopropoxide), acid salts (for example, sodium hydrogen carbonate, potassium hydrogen carbonate, monopotassium dihydrogen phosphate, monoammonium dihydrogen phosphate, potassium hydrogen sulfate, etc.), etc.

While the amount of these salts to be present in the reaction mixture may be selected conveniently, the salt to be concomitantly present with both the reactants may ordinarily be used, with respect to cyanoacetylene, within the range of about 0.1 to 20 mole percent.

The isolation of the objective compound, maleonitrile, requires no complicated procedure, because of the concomitant presence of less by-products in the reaction mixture. Thus, to isolate the objective compound from the reaction system, use is made singly or in combination of per se conventional procedures such as distillation, recrystallization, column chromatography, extraction, etc.

As the starting material cyanoacetylene, there may conveniently be used any one produced through known processes. One of such known processes is exemplified here. Namely, it is produced in a good yield through a thermal reaction of acrylonitrile with chlorine in gaseous phase (German Patent Publication DT-OLS 1,940,705).

For further detailed explanation of the invention, the following examples, which are not limitative but illustrative as to the scope of this invention, are given, wherein the term "part(s)" means "weight part(s)", unless otherwise noted and the relationship between "part(s)" and "part(s) by volume" corresponds to that between "gram(s)" and "milliliter(s)".

EXAMPLE 1

A hermetically-sealable vessel of 200 parts by volume capacity was filled with 10.2 parts of cyanoacetylene, 6.5 parts of liquid hydrogen cyanide and 40 parts by volume of acetonitrile. The reaction vessel was cooled with ice-water. To the vessel was added 0.1 part of potassium cyanide and the reaction mixture was stirred at the same temperature as above for 2 hours. The vessel was stoppered and the mixture was allowed to react at room temperature overnight. Then, the low-boiling fractions were distilled off under reduced pressure to obtain 16.5 parts of a crude reaction product.

A gas-chromatographic assay of this product using silicone DC-550-stearic acid as a filler revealed that the product was almost exclusively comprised of maleonitrile, with about 1% of fumaronitrile as a contaminant. To purify the product further, it was subjected to column chromatography on silica gel with chloroform as the solvent. The procedure yielded 12.7 parts of pure maleonitrile melting at 32°C. Percent yield 81.5.

EXAMPLE 2

The reaction was carried out in the same manner as Example 1 except that it was conducted under stirring on a water bath at about 65°C to 70°C for 7 hours in the absence of potassium cyanide. The procedure yielded maleonitrile in a yield of 60%.

EXAMPLE 3

The reaction was carried out in the same manner as Example 1, except that 0.2 part each of the agents indicated below were used in place of 0.1 part of potassium cyanide. The procedures yielded maleonitrile in the yields shown below. There are cases in which the indicated yields can be improved by modifying or selecting reaction conditions (reaction temperature, reaction time, type and amount of solvent, etc.)

| Agent added | Yield of maleonitrile | Percentage (relative to maleonitrile) of concomitant fumaronitrile as determined by gas chromatography |
|---|---|---|
| a) Tetraethylammonium chloride | 71 | 4.8 |
| b) Tetraethylammonium bromide | 78 | 8.6 |
| c) Tetraethylammonium iodide | 82 | 2.6 |
| d) Benzyltrimethyl-ammonium chloride | 80 | 3.3 |
| e) Benzyltrimethyl-ammonium bromide | 87 | 5.2 |
| f) Benzyltrimethyl-ammonium iodide | 87 | 1.1 |
| g) Potassium thiocyanate | 82 | 1.2 |
| h) Lithium chloride | 82 | (Trace) |
| i) Lithium bromide | 85 | 5.8 |
| g) Potassium fluoride | 73 | 6.8 |
| k) Potassium iodide | 92 | 1.0 |
| l) Potassium formate | 71 | 2.3 |
| m) Potassium acetate | 70 | (Trace) |
| n) Sodium carbonate | 74 | 0.0 |
| o) Lithium hydroxide monohydrate | 82 | 1.9 |

What we claim is:

1. A method for producing maleonitrile, which comprises reacting cyanoacetylene with hydrogen cyanide in an organic solvent.

2. A method according to claim 1, wherein the organic solvent is selected from the group consisting of acetonitrile, methylene chloride, chloroform, diethyl ether, tetrahydrofuran, dioxane, ethyl acetate, acetic acid, dimethylformamide, dimethylsulfoxide and benzene.

3. A method according to claim 2, wherein the organic solvent is acetonitrile.

4. A method according to claim 1, wherein the reaction is conducted at a temperature ranging from about −20°C to 100°C.

5. A method according to claim 1, wherein the reaction is conducted in the presence of a catalyst.

6. A method according to claim 5, wherein the catalyst is selected from the group consisting of a Lewis acid, an alkali metal hydroxide, an alkali metal halide, a quaternary ammonium salt, and a mineral acid salt of an alkali metal.

7. A method according to claim 6, wherein the Lewis acid is anhydrous aluminium chloride or potassium bifluoride.

8. A method according to claim 6, wherein the alkali metal hydroxide is lithium hydroxide.

9. A method according to claim 6, wherein the alkali metal halide is lithium chloride, lithium bromide, potassium iodide or potassium fluoride.

10. A method according to claim 6, wherein the quaternary ammonium salt is tetraethylammonium chloride, tetraethylammonium bromide, tetraethylammonium iodide, benzyltrimethylammonium chloride, benzyltrimethylammonium bromide or benzyltrimethylammonium iodide.

11. A method according to claim 6, wherein the mineral acid salt of an alkali metal is potassium cyanide, potassium thiocyanate or sodium carbonate.

* * * * *